United States Patent
Chen et al.

(10) Patent No.: US 8,535,724 B2
(45) Date of Patent: Sep. 17, 2013

(54) COMPOSITIONS CONTAINING RESVERATROL AND PECTIN

(75) Inventors: Chyi-Cheng Chen, Binningen (CH); Sui-Kchen Chen, legal representative, Taipei (TW); Sylvain Diguet, Hagenthal-le-Haut (FR); Bruno H. Leuenberger, Rheinfelden (CH); Kai Urban, Bad Säckingen (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/740,154

(22) PCT Filed: Oct. 10, 2008

(86) PCT No.: PCT/EP2008/008561
§ 371 (c)(1), (2), (4) Date: Sep. 29, 2010

(87) PCT Pub. No.: WO2009/056212
PCT Pub. Date: May 7, 2009

(65) Prior Publication Data
US 2011/0039945 A1    Feb. 17, 2011

(30) Foreign Application Priority Data
Oct. 29, 2007   (EP) .................................. 07021099

(51) Int. Cl.
*A61K 9/14* (2006.01)

(52) U.S. Cl.
USPC ........................................................ 424/489

(58) Field of Classification Search
None
See application file for complete search history.

(56) References Cited

U.S. PATENT DOCUMENTS

| | | | | |
|---|---|---|---|---|
| 4,826,793 | A * | 5/1989 | Velten et al. | 502/64 |
| 5,707,959 | A * | 1/1998 | Pancheri et al. | 510/444 |
| 6,270,780 | B1 * | 8/2001 | Carson et al. | 424/401 |
| 2001/0005514 | A1 * | 6/2001 | Chen et al. | 424/736 |
| 2003/0152617 | A1 * | 8/2003 | Yatvin | 424/450 |
| 2004/0063648 | A1 * | 4/2004 | Pandol et al. | 514/27 |
| 2004/0108608 | A1 * | 6/2004 | Ju et al. | 264/4.1 |
| 2004/0108609 | A1 * | 6/2004 | Pham | 264/4.6 |
| 2005/0008692 | A1 * | 1/2005 | Chen et al. | 424/464 |
| 2005/0013854 | A1 * | 1/2005 | Mannino et al. | 424/450 |
| 2005/0026849 | A1 * | 2/2005 | Singh et al. | 514/26 |
| 2005/0267209 | A1 * | 12/2005 | Peterson et al. | 514/554 |
| 2006/0013850 | A1 * | 1/2006 | Domb | 424/422 |
| 2006/0013870 | A1 * | 1/2006 | Kuhrts | 424/464 |
| 2006/0292081 | A1 * | 12/2006 | Morton et al. | 424/46 |
| 2007/0077279 | A1 * | 4/2007 | Schweikert et al. | 424/440 |
| 2008/0090897 | A1 * | 4/2008 | Steiner et al. | 514/453 |
| 2008/0193575 | A1 * | 8/2008 | Chen et al. | 424/757 |
| 2008/0213433 | A1 * | 9/2008 | Feller et al. | 426/73 |

FOREIGN PATENT DOCUMENTS

| | | |
|---|---|---|
| EP | 1110550 A2 * | 6/2001 |
| WO | 99/48386 | 9/1999 |
| WO | 03/011339 | 2/2003 |
| WO | WO 2004112491 A2 * | 12/2004 |
| WO | 2006/087164 | 8/2006 |
| WO | 2007/096078 | 8/2007 |
| WO | WO 2009/056212 | 5/2009 |

OTHER PUBLICATIONS

International Search Report for PCT/EP2008/008561, mailed Mar. 27, 2009.

* cited by examiner

*Primary Examiner* — Robert A Wax
*Assistant Examiner* — Olga V Tcherkasskaya
(74) *Attorney, Agent, or Firm* — Nixon & Vanderhye P.C.

(57) ABSTRACT

The present invention relates to compositions, preferably in the form of a powder and/or granules, which contain resveratrol and pectin, and a process for the manufacture of such compositions.

21 Claims, 1 Drawing Sheet

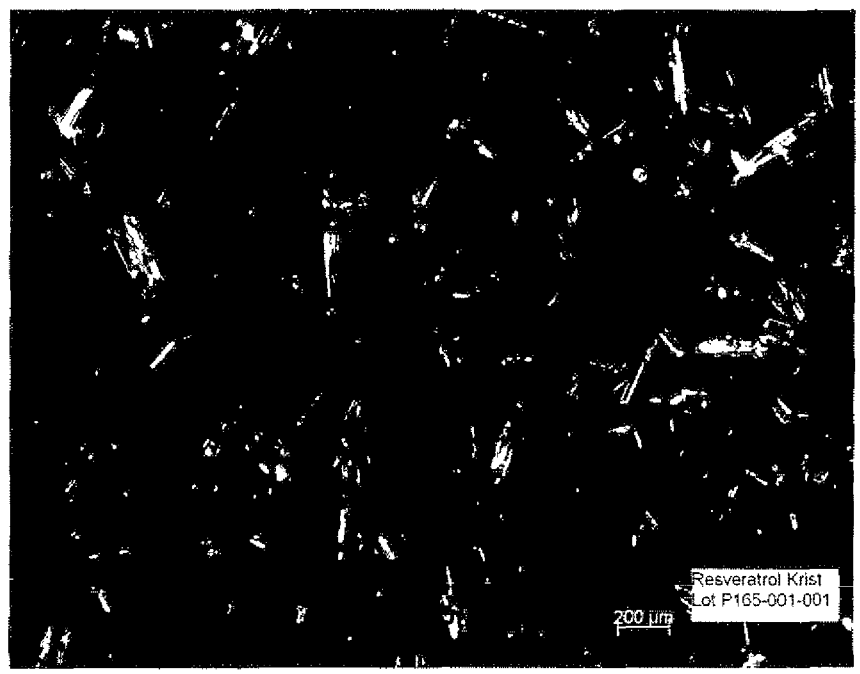

COMPOSITIONS CONTAINING RESVERATROL AND PECTIN

This application is the U.S. national phase of International Application No. PCT/EP2008/008561, filed 10 Oct. 2008, which designated the U.S. and claims priority to European Application No. 07021099.2, filed 29 Oct. 2007, the entire contents of each of which are hereby incorporated by reference.

The present invention relates to compositions comprising resveratrol and pectin. The present invention further relates to a process for the manufacture of such compositions, and to their use in dietary supplements, pharmaceutical and personal care compositions. The present invention is also directed to the use of pectin for improving the flowability of a powder containing resveratrol.

Resveratrol is a phytoalexin produced naturally by several plants when under attack by bacteria or fungi. Phytoalexins are antibacterial and anti-fungal chemicals produced by plants as a defense against infection by pathogens. A number of beneficial health effects, such as anti-cancer, antiviral, neuroprotective, anti-aging, anti-inflammatory and life-prolonging effects have been reported.

The term "resveratrol" as used herein relates to resveratrol, whereas the carbon-carbon double bond may be trans or cis and includes cis/trans mixtures. Especially preferred for the purposes of the invention is (trans)-resveratrol. The term "resveratrol" as used herein encompasses synthetic resveratrol as well as natural extracts as well as concentrates obtained by chemically (especially enzymatically), thermally, physically and/or by UV radiation treated material.

Resveratrol is usually obtainable as crystalline powder consisting of resveratrol needles (see FIG. 1) which has a very poor flowability. The poor flowability renders the crystalline powder difficult for use in making tablets and other application forms that require the powder to be free flowing.

Compositions known in the art which have solved a similar problem are compositions of polysaccharides with compounds such as (−)-epigallocatechin gallate (WO 03/011339) and genistein (WO 2006/087164), where the flowability of the compounds was improved by the addition of a polysaccharide. (−)-Epigallocatechin gallate is water-soluble, whereas genistein is generally hardly or essentially not water-soluble.

The process known in the art is not applicable to resveratrol. This process consists of fluidizing the crystals in a hot air flow and spraying on an aqueous pectin solution. The spraying of 1 to 2 wt.-% of pectin (based on dry matter) results in a product that may be used in making tablets etc. Because resveratrol crystals have a very low flowability they cannot be fluidized properly and the granulation process can accordingly not be carried our satisfactorily (see also Comparative Example 1).

It was therefore an objective of the following invention to provide a composition containing resveratrol which shows improved flowability and a process for the manufacture of such a composition.

It has surprisingly been found that the objective of the present invention is achieved by a composition containing resveratrol and pectin.

Preferably the composition is in the form of a powder or granules. In each granule or powder particle, one or more resveratrol crystals are coated or partially coated with pectin. The coated or partially coated crystal or crystals are held (glued) together by pectin, which functions as a binder, to form a granule with appropriate size.

The preferred particle size distribution of the composition of the present invention, preferably in form of a powder or of granules, is as follows:
at least 95% of the particles have a size of ≦1500 μm (preferred: ≦1000 μm, more preferred ≦850 μm), whereby at most 35% of the particles have a size of ≦50 μm (preferred: ≦100 μm, more preferred ≦150 μm).

In another preferred embodiment of the present invention particle size distribution of the composition of the present invention, preferably in form of a powder or of granules, is as follows:
at least 95% of the particles have a size in the range of from 10 μm to 1500 μm (preferred: in the range of from 10 μm to 1000 μm, more preferred in the range of from 10 μm to 850 μm), whereby at most 35% of the particles have a size in the range of from 10 μm to 50 μm (preferred: in the range of from 10 μm to 100 μm, more preferred in the range of from 10 μm to 150 μm).

The composition according to the present invention has preferably a water activity of from 0.05 to 0.7, preferably of from 0.1 to 0.5, more preferably of from 0.2 to 0.5. The water activity is measured using a Novasina Thermoconstanter TH200 (Novasina AG, Zürich, Switzerland).

According to the present invention it is advantageous if the moisture content in the composition is in the range of from 0 to 6 weight-%, preferred from 0 to 3 weight-%, each based on the total weight of the composition.

Preferably the used resveratrol crystals have needle dimensions within the following ranges:
Length (L): 200 to 800 μm
Thickness (D): 5 to 100 μm
Form factor (L/D): 5 to 30.

Pectin is a polysaccharide and described for example in the book entitled Industrial Gums, third edition, Academic Press, Inc., 1993, pages 257ff. as well as in EP-A 1 110 550. Pectins used in the present invention are generally commercially available and e.g. produced from citrus peel or apple (pomace). Other possible sources are sugarbeet, sunflower and mango. Preferred pectins to be used within the scope of the present invention are citrus pectins, which generally have lighter colour than apple pectins and, thus, do not contribute significant colour to the final product.

In an embodiment of the invention high molecular weight pectin may be used. The term "high molecular weight pectin" as used herein denotes pectin having a molecular weight of more than about 300 kDalton. The preferred high molecular weight pectins are those having a molecular weight of from about 300 kDalton to about 400 kDalton, particularly 350 kDalton. Such pectins can be obtained as disclosed in U.S. Pat. No. 6,143,337 the contents of which are incorporated herein by reference. The molecular weight is determined by size exclusion chromatography having a multi angle laser light scattering detector as described in U.S. Pat. No. 6,143,337. However, pectins of higher molecular weight, e.g. up to 2.000 kDalton can be used also in the present invention. Pectins of such molecular weight can be obtained e.g. from Asteraceae plants, especially cichory and Jerusalem artichoke, see WO 99/03892. Fractions of the desired high molecular weight can be obtained from such pectins by membrane filtration, e.g. using polyethersulfone or composite regenerate cellulose membranes as supplied by Millipore Corporation, Bedford, Mass. 01730, USA, under the trade name Pellicon® Tangential Flow Filtration Cassettes.

In a preferred embodiment of the composition of the present invention the pectin is used in an amount of from 0.1% to 15% by weight, more preferably from 0.5% to 7% by weight, most preferably from 1.5% to 5% by weight, each based on the total weight of the composition.

In a further aspect, the present invention relates to a process for the manufacture of the composition of the present invention.

Manufacture of the Composition

The composition of this invention may be produced by any method known per se for the production of powders or granules. Preferred methods are fluidized-bed granulation, high-shear granulation, extrusion, spray-drying and wet granulation. The present invention is also directed to process for the manufacture of a composition of the present invention by those methods.

For obtaining the composition of the present invention by spray-drying it is convenient to prepare a slurry of all components in a solvent or solvent mixture which is able to dissolve the pectin. An especially preferred solvent is water. The slurry has preferably a solid content of 10 to 70% by weight, preferably of 25 to 50% by weight, each based on the total weight of the slurry. The slurry is then spray-dried in a manner known per se.

Thus another aspect of the present invention is a process for the manufacture of a composition as mentioned above, which comprises preparing a slurry, preferably an aqueous slurry, of all solid components, preferably having a solid content of 10 to 70% by weight, preferably 25 to 50% by weight, each based on the total weight of the slurry, and spray-drying the slurry in a manner known per se.

Fluidized-bed granulation is an especially preferred process for the manufacture of a composition according to the present invention. It is preferred to use a known fluidized-bed granulating apparatus which comprises a fluidized-bed drying device fitted with spray means, Preferably resveratrol forms the fluidized bed, the fluidized bed being fluidized by air or an inert gas, e.g. nitrogen. The pectin is dissolved in an appropriate amount of water or solvent (mixture) capable of dissolving the pectin, preferably in an appropriate amount of water, and sprayed in the form of an atomized mist onto the fluidized particles in such a manner that the granulating and drying operations is accomplished in a single step.

Alternatively, the pectin can be mixed with resveratrol and the fluidized bed being fluidized by air or an inert gas, e.g. nitrogen. An appropriate amount of water or solvent (mixture) capable of dissolving pectin, preferably an appropriate amount of water, is sprayed in the form of an atomized mist onto the fluidized particles in such a manner that the granulating and drying operations is accomplished in a single step. The granulating process is continued until the desired granule or powder is obtained.

At the end of the granulation process, the granules may be sieved to fractionate the granules as to size. While the particle size is not narrowly critical to the invention it is, for practical purposes, preferably within 50 and 1500 μm, more preferably between 100 and 1000 μm, most preferably from 150 to 850 μm.

In an especially preferred embodiment of the present invention the resveratrol crystals are milled before the fluidizing step. The milling step is preferably carried out in a commercially available high shear vessel. The desired mean particle size of the resveratrol crystals after the milling step is in the range of 100 to 400 μm with regard to the length of the needles and may be achieved by adjusting the impeller running speed and impeller running time with respect to each other. The preferred milling parameters may differ depending on the high shear vessel used in the milling step, but can easily be adjusted by the person skilled in the art through no inventive fault of his own.

In a further preferred embodiment of the process of the present invention one or more flow-conditioning agents (also referred to as anti-caking agents, flow enhancer) are added to the resveratrol crystals before the fluidizing step. Preferred flow-conditioning agents are for example (hydrophilic) fumed silica, such as those commercially available under the trade name AEROSIL® from Degussa.

According to the present invention it is advantageous if the amount of flow-conditioning agent(s) (one or more compounds) in the composition is in the range of from 0.1 to 1% by weight, based on the total weight of the composition.

Therefore, a further aspect of the present invention is a process for the manufacture of a composition as mentioned above, which comprises forming a fluidized bed of resveratrol with or without pectin within a fluidized-bed drying device fitted with spray means, said fluidized bed being fluidized by air or an inert gas, and spraying a solution, preferably an aqueous solution, of pectin or only water or the solvent (mixture) in the form of an atomized mist onto the fluidized particles until the desired granule or powder is obtained.

The composition thus obtained may be further processed depending on the intended use of resveratrol and/or the desired applications. For instance, the composition may be compressed into tablets with conventional tabletting methods and machinery.

Optionally the compositions, preferably the powder or the granules, may further be mixed with a lubricant or a mixture of lubricants and then compressed into tablets. If additional lubricant is used it is preferably selected from the group of stearic acid or the magnesium or calcium salt thereof, or glyceryl behenate 45 (Compritol 888 ATO), preferably in an amount of 0.5 to 4% by weight, based on the total weight of the composition.

Alternatively or additionally the composition may be mixed with excipients. Examples of excipients are (microcrystalline or powdered) cellulose, (pregelatinized) starch, lactose (anhydrous or monohydrate), sorbitol, mannitol, calcium carbonate, dibasic calcium phosphate (dehydrate), tribasic calcium phosphate, calcium sulphate, dextrates, dextrin, dextrose, fructose, kaolin, lactitol and (dextrinized) sucrose. Dextrinized sucrose is e.g. commercially available under the trade name Di Pac® sugar from Tate and Lyle North American Sugars, Inc., Canada, or from Domino Specialty Ingredients, Baltimore, Md., USA.

The composition of the present invention may also be mixed with adjuvants.

Furthermore the present invention is directed to dosage forms based on a composition according to the present invention comprising resveratrol and pectin, such as tablets, pills, granules, dragees, capsules, and effervescent formulations such as powders and tablets. Preferably the dosage form is a tablet.

Further object of the present invention are dietary as well as pharmaceutical and personal care compositions comprising resveratrol and pectin.

The term "dietary compositions" comprises any type of (fortified) food/feed and beverages including also clinical nutrition, and also dietary supplements.

Beverages wherein the composition of the present invention can be used as an ingredient can be carbonated beverages e.g., flavoured seltzer waters, soft drinks or mineral drinks, as well as non-carbonated beverages e.g. flavoured waters, fruit juices, fruit punches and concentrated forms of these beverages. They may be based on natural fruit or vegetable juices or on artificial flavours. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the composition of the present invention can be used as an ingredient. Typical examples of such products are milk drinks, ice cream, cheese, yoghurt and the like. Milk replacing products such as soymilk drinks and tofu products are also comprised within this range of application.

Also included are sweets which contain the composition of the present invention as an ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the composition of the present invention as an ingredient. Furthermore, fruit preparations used for dairy and cereals are also included.

Pharmaceutical compositions such as tablets such as chewable tablets, effervescent tablets or film-coated tablets or capsules such as hard shell capsules wherein the compositions are used as an ingredient are also within the scope of the present invention. The product forms are typically added as powders to the tabletting mixture or filled into the capsules in a manner per se known for the production of capsules.

Animal feed products such as premixes of nutritional ingredients, compound feeds, milk substitutes, liquid diets or feed preparations wherein the compositions are used as an ingredient are also within the scope of the present invention.

Examples of personal care compositions according to the present invention are cosmetics, toiletries and derma products. Therefore, skin and hair care products such as creams, lotions, baths, lipsticks, shampoos, conditioners, sprays or gels wherein the compositions are used as an ingredient are also within the scope of the present invention.

In still another aspect, the invention is concerned with the use of pectin for improving the flowability of a powder of resveratrol. Or in other words the present invention is also directed to the use of pectin as granulating agent for compositions containing resveratrol.

The invention is illustrated by FIG. 1:

FIG. 1 shows the typical needle form of resveratrol crystals.

The invention is illustrated further by the following Examples.

EXAMPLES

Example 1

796 g resveratrol and 4 g Aerosil 200 are placed in a 4 liter Diosna high shear vessel at room temperature. The mix is agitated 10 minutes with the impeller running at 500 rpm and 10 more minutes with the impeller running at 1000 rpm. The product is discharged and passed through a 600 μm sieve.

300 g of the milled resveratrol are placed in the DMR fluid bed vessel and fluidized with 30 m³/h air at 60° C. A 2.5% pectin solution in water is sprayed at a rate in a range for 2.5 to 5 g/min onto the fluidized powder. 380 g of the solution is sprayed. The product is then dried until the product temperature reaches 40° C.

Comparative Example 1

300 g of resveratrol crystals (not milled) are placed in the DMR fluid bed vessel with 30 m³/h air at 60° C. No fluidization can be obtained. The spraying of a 2.5% solution sticks the product onto the wall. The desired granules cannot be obtained.

The invention claimed is:

1. A process for the manufacture of a flowable powder or flowable granules comprising resveratrol and pectin, which comprises the steps of:
    milling resveratrol crystals in a high shear vessel in order to achieve a mean particle size of the resveratrol crystals after the milling step in the range of 100 to 400 μm with regard to the length of the needles;
    preparing a slurry of said milled resveratrol and pectin, said slurry having a solid content of 10 to 70% by weight, based on the total weight of the slurry, and
    spray-drying the slurry to obtain the powder or granules comprising resveratrol and pectin.

2. A process for the manufacture of a flowable powder or flowable granules comprising resveratrol and pectin, which comprises the steps of:
    milling resveratrol crystals in a high shear vessel in order to achieve a mean particle size of the resveratrol crystals after the milling step in the range of 100 to 400 μm with regard to the length of the needles;
    forming a fluidized bed of said milled resveratrol within a fluidized-bed drying device which includes a sprayer, wherein the fluidized bed is fluidized by air or an inert gas, and
    spraying an aqueous solution of pectin in the form of an atomized mist onto the fluidized particles until the desired granule or powder is obtained.

3. A process for the manufacture of a flowable powder or flowable granules comprising resveratrol and pectin, which comprises the steps of:
    milling resveratrol crystals in a high shear vessel in order to achieve a mean particle size of the resveratrol crystals after the milling step in the range of 100 to 400 μm with regard to the length of the needles;
    forming a fluidized bed of said milled resveratrol with pectin within a fluidized-bed drying device which includes a sprayer, wherein the fluidized bed is fluidized by air or an inert gas, and
    spraying water in the form of an atomized mist onto the fluidized particles until the desired granule or powder is obtained.

4. A process according to claim 2 or 3, further comprising adding at least one flow-conditioning agent to the composition before forming the fluidized bed.

5. A composition in the form of a flowable powder or flowable granules obtained by a process according to claim 4.

6. A composition comprising flowable, powder or flowable granules obtained by a process according to any one of claims 1 to 3.

7. The composition according to claim 6, wherein the amount of pectin is in the range of from 0.1% to 15% by weight, based on the total weight of the composition.

8. The composition according to claim 6, further comprising at least one ore flow-conditioning agent.

9. The composition according to claim 8, wherein the amount of flow-conditioning agent is in the range of from 0.1 to 1% by weight, based on the total weight of the composition.

10. A dosage form which comprises a composition as claimed in claim 6.

11. The dosage form according to claim 10, wherein the dosage form is a tablet.

12. Dietary, pharmaceutical and personal care compositions comprising a composition as claimed in claim 6.

13. The process of claim 1 wherein at least 95% of the flowable powder or flowable granules have a size of $\leq$1500 μm and at most 35% of the particles have a size of $\leq$50 μm.

14. The process of claim 1 wherein at least 95% of the flowable powder or flowable granules have a size of $\leq$1000 μm and at most 35% of the particles have a size of $\leq$100 μm.

15. The process of claim 1 wherein at least 95% of the flowable powder or flowable granules have a size of $\leq$850 μm and at most 35% of the particles have a size of $\leq$150 μm.

16. The process of claim 2 wherein at least 95% of the flowable powder or flowable granules have a size of $\leq$1500 μm and at most 35% of the particles have a size of $\leq$50 μm.

17. The process of claim 2 wherein at least 95% of the flowable powder or flowable granules have a size of $\leq$1000 μm and at most 35% of the particles have a size of $\leq$100 μm.

18. The process of claim 2 wherein at least 95% of the flowable powder or flowable granules have a size of $\leq$850 μm and at most 35% of the particles have a size of $\leq$150 μm.

19. The process of claim 3 wherein at least 95% of the flowable powder or flowable granules have a size of $\leq$1500 μm and at most 35% of the particles have a size of $\leq$50 μm.

20. The process of claim 3 wherein at least 95% of the flowable powder or flowable granules have a size of $\leq$1000 μm and at most 35% of the particles have a size of $\leq$100 μm.

21. The process of claim 3 wherein at least 95% of the flowable powder or flowable granules have a size of $\leq$850 μm and at most 35% of the particles have a size of $\leq$150 μm.

\* \* \* \* \*